US012697417B2

(12) United States Patent
Luxenhofer et al.

(10) Patent No.: US 12,697,417 B2
(45) Date of Patent: Aug. 4, 2026

(54) INVERSE THERMOGELLING POLYOXAZOLINE COPOLYMERS

(71) Applicant: Julius-Maximilians-Universität Würzburg, Würzburg (DE)

(72) Inventors: Robert Luxenhofer, Würzburg (DE); Lukas Hahn, Würzburg (DE)

(73) Assignee: Julius-Maximilians-Universität Würzburg, Würzburg (DE)

( * ) Notice: Subject to any disclaimer, the term of this patent is extended or adjusted under 35 U.S.C. 154(b) by 387 days.

(21) Appl. No.: 18/281,974

(22) PCT Filed: Mar. 22, 2022

(86) PCT No.: PCT/EP2022/057509
§ 371 (c)(1),
(2) Date: Sep. 14, 2023

(87) PCT Pub. No.: WO2022/200360
PCT Pub. Date: Sep. 29, 2022

(65) Prior Publication Data

US 2024/0299627 A1 Sep. 12, 2024

(30) Foreign Application Priority Data

Mar. 25, 2021 (EP) .................................... 21164966

(51) Int. Cl.

| | |
|---|---|
| ***A61L 27/52*** | (2006.01) |
| ***A61L 27/18*** | (2006.01) |
| ***B29C 64/40*** | (2017.01) |
| ***B29K 96/04*** | (2006.01) |
| ***B29K 105/00*** | (2006.01) |
| ***B29K 105/16*** | (2006.01) |
| ***B33Y 70/00*** | (2020.01) |
| ***B33Y 80/00*** | (2015.01) |
| ***C08G 73/02*** | (2006.01) |
| ***C08J 3/075*** | (2006.01) |

(52) U.S. Cl.
CPC ............... *A61L 27/52* (2013.01); *A61L 27/18* (2013.01); *B29C 64/40* (2017.08); *B33Y 70/00* (2014.12); *B33Y 80/00* (2014.12); *C08G 73/0233* (2013.01); *C08J 3/075* (2013.01); *B29K 2096/04* (2013.01); *B29K 2105/0061* (2013.01); *B29K 2105/0085* (2013.01); *B29K 2105/16* (2013.01); *C08J 2379/02* (2013.01); *C08J 2379/04* (2013.01)

(58) Field of Classification Search
CPC ......... A61L 27/52; A61L 27/18; B29C 64/40; B33Y 70/00; B33Y 80/00; C08G 73/0233; C08J 3/075; C08J 2379/04; C08J 2379/02; B29K 2096/04; B29K 2105/0061; B29K 2105/0085; B29K 2105/16
See application file for complete search history.

(56) References Cited

U.S. PATENT DOCUMENTS

2019/0153157 A1 5/2019 Lorson et al.
2021/0087338 A1* 3/2021 Luxenhofer ............. C08J 3/075

FOREIGN PATENT DOCUMENTS

EP 3789424 A1 3/2021

OTHER PUBLICATIONS

Birch et al: Thermal-Responsive Behavior of a Cell Compatible Chitosan/Pectin Hydrogel. Biomacromolecules, 2015, vol. 16, No. 6, pp. 1837-1843.
Bokias et al: Synthesis and Aqueous Solution Properties of Novel Thermoresponsive Graft Copolymers Based on a Carboxymethylcellulose Backbone. Macromolecules, 2001, vol. 34, No. 14, pp. 4958-4964.
Bonné et al: Aggregation behavior of amphiphilic poly(2-alkyl-2-oxazoline) diblock copolymers in aqueous solution studied by fluorescence correlation spectroscopy. Colloid and Polymer Science, 2004, vol. 282, pp. 833-843.
Bonné et al: Effect of Polymer Architecture of Amphiphilic Poly(2-oxazoline) Copolymers on the Aggregation and Aggregate Structure. Macromolecular Chemistry and Physics, Jul. 2007, vol. 208, pp. 1402-1408.
Chimene et al: Hydrogel Bioink Reinforcement for Additive Manufacturing: A Focused Review of Emerging Strategies. Advanced Materials, 2020, vol. 32, No. 1, 1902026.
Dargaville et al: Poly(2-oxazoline) Hydrogels: State-of-the-Art and Emerging Applications. Macromolecular Bioscience, 2018, vol. 18, No. 6, 1800070.

(Continued)

*Primary Examiner* — Rabon A Sergent
(74) *Attorney, Agent, or Firm* — Mark W. Scott; Laine IP Oy

(57) ABSTRACT

Provided is a block copolymer comprising a polymer block (A) which comprises repeating units of formula (I) and a polymer block (B) which comprises repeating units of formula (II), (I)

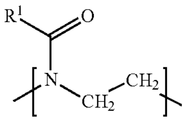

(II)

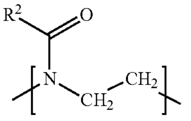

wherein $R^1$ is methyl or ethyl, and $R^2$ represents a group —$CH_2$—$CH_2$-phenyl. The copolymer of the present invention allows a rapid thermoresponsive inverse gelation to be achieved, yielding a hydrogel with viscoelastic solid-like properties, as well as shear thinning, rapid structure recovery and good strain resistance properties. The hydrogel can be favorably used in 3D printing applications.

15 Claims, 5 Drawing Sheets

(56) References Cited

OTHER PUBLICATIONS

Djabourov et al: Gelation of Aqueous Gelatin Solutions. II. Rheology of the sol-gel transition. J. Phys. France, 1988, vol. 49, pp. 319-332.
Glassner et al: Poly(2-oxazoline)s: A comprehensive overview of polymer structures and their physical properties. Polymer International, Jan. 2018, vol. 67, No. 1, pp. 32-45.
Groll et al: A definition of bioinks and their distinction from biomaterial inks. Biofabrication, 2019, vol. 11, No. 1, 013001.
Groll et al: Biofabrication: reappraising the definition of an evolving field. Biofabrication, 2016, vol. 8, 013001.
Gupta et al: Synthesis and characterization of PEPO grafted carboxymethyl guar and carboxymethyl tamarind as new thermo-associating polymers. Carbohydrate Polymers, Mar. 6, 2015, vol. 117, pp. 331-338.
Hahn et al: Inverse Thermogelation of Aqueous Triblock Copolymer Solutions into Macroporous Shear-Thinning 3D Printable Inks. ACS Applied Materials & Interfaces, 2020, vol. 12, No. 11, pp. 12445-12456.
Hahn et al: Investigating the Influence of Aromatic Moieties on the Formulation of Hydrophobic Natural Products and Drugs in Poly(2-Oxazoline)-Based Amphiphiles. Biomacromolecules, 2018, vol. 19, No. 7, pp. 3119-3128.
Harris et al: Tuning drug release from polyoxazoline-drug conjugates. European Polymer Journal, Nov. 2019, vol. 120, 109241.
Koonar et al: ABC triblock terpolymers exhibiting both temperature- and ph-sensitive micellar aggregation and gelation in aqueous solution. Langmuir, Dec. 21, 2012, vol. 28, No. 51, pp. 17785-17794.
Lorson et al: A Thermogelling Supramolecular Hydrogel with Sponge-Like Morphology as a Cytocompatible Bioink. Biomacromolecules, 2017, vol. 18, No. 7, pp. 2161-2171.
Lorson et al: Poly(2-oxazoline)s based biomaterials: A comprehensive and critical update. Biomaterials, Sep. 2018, vol. 178, pp. 204-280.
Luxenhofer et al: Click Chemistry with Poly(2-oxazoline)s. Macromolecules, 2006, vol. 39, No. 10, pp. 3509-3516.
Lübtow et al: Drug Specificity, Synergy and Antagonism in Ultrahigh Capacity Poly(2-Oxazoline)/Poly(2-Oxazine) Based Formulations. Journal of the American Chemical Society, 2017, vol. 139, No. 32, pp. 10980-10983.
Lübtow et al: Temperature-Dependent Rheological and Viscoelastic Investigation of a Poly(2-Methyl-2-Oxazoline)-B-Poly(2-Iso-Butyl-2-Oxazoline)-B-Poly(2-Methyl-2-Oxazoline)-Based thermogelling Hydrogel. Journal of Functional Biomaterials, 2019, vol. 10, No. 3, 36.
Malda et al: 25th Anniversary Article: Engineering Hydrogels for Biofabrication. Advanced Materials, 2013, vol. 25, No. 36, pp. 5011-5028.
Meiswinkel et al: A New Type of Thermoresponsive Copolymer with UCST-Type Transitions in Water: Poly(N-vinylimidazole-co-1-vinyl-2-(hydroxymethyl)imidazole). Macromolecular Rapid Communications, Jun. 25, 2013, vol. 34, No. 12, pp. 1026-1031.
Monnery et al: Thermoresponsive hydrogels formed by poly(2-oxazoline) triblock copolymers. Polymer Chemistry, 2019, vol. 10, No. 25, pp. 3480-3487.
Moreadith et al: Clinical development of a poly(2-oxazoline) (POZ) polymer therapeutic for the treatment of Parkinson's disease—Proof of concept of POZ as a versatile polymer platform for drug development in multiple therapeutic indications. European Polymer Journal, Mar. 2017, vol. 88, pp. 524-552.
Paxton et al: Proposal to Assess Printability of Bioinks for Extrusion-Based Bioprinting and Evaluation of Rheological Properties Governing Bioprintability. Biofabrication, 2017, vol. 9, No. 4, 044107.
Plunkett et al: PNIPAM Chain Collapse Depends on the Molecular Weight and Grafting Density. Langmuir, 2006, vol. 22, No. 9, pp. 4259-4266.
Ribeiro et al: Assessing Bioink Shape Fidelity to Aid Material Development in 3d Bioprinting. Biofabrication, 2017, vol. 10, No. 1, 014102.
Sedlacek et al: Drug Delivery Systems Based on Poly(2-Oxazoline)s and Poly(2-Oxazine)s. Advanced Therapeutics, 2020, vol. 3, No. 1, 1900168.
Seuring et al: Non-Ionic Homo- and Copolymers with H-Donor and H-Acceptor Units with an UCST in Water. Macromolecular Chemistry and Physics, Oct. 1, 2010, vol. 211, No. 19, pp. 2109-2117.
Seuring et al: Upper Critical Solution Temperature of Poly(N-acryloyl glycinamide) in Water: A Concealed Property. Macromolecules, 2012, vol. 45, No. 1, pp. 374-384.
Shimada et al: Ureido-Derivatized Polymers Based on Both Poly(allylurea) and Poly(l-citrulline) Exhibit UCST-Type Phase Transition Behavior under Physiologically Relevant Conditions. Biomacromolecules, 2011, vol. 12, No. 10, pp. 3418-3422.
Sood et al: Stimuli-Responsive Hydrogels in Drug Delivery and Tissue Engineering. Drug Delivery. 2016, vol. 23, No. 3, pp. 748-770.
Taribagil et al: Hydrogels from ABA and ABC Triblock Polymers. Macromolecules, 2010, vol. 43, No. 12, pp. 5396-5404.
Valot et al: Chemical insights into bioinks for 3D printing. Chemical Society Reviews, 2019, vol. 48, No. 15, pp. 4049-4086.
Witte et al: Simple Synthesis of 2-Substituted 2-Oxazolines and 5,6-Dihydro-4h-1,3-Oxazines. Angewandte Chemie International Edition in English, 1972, vol. 11, No. 4, pp. 287-288.
Zhang et al: Thermoresponsive polymers with lower critical solution temperature: from fundamental aspects and measuring techniques to recommended turbidimetry conditions. Materials Horizons, 2017, vol. 4, No. 2, pp. 109-116.

* cited by examiner

INVERSE THERMOGELLING POLYOXAZOLINE COPOLYMERS

Thermosensitive water-soluble polymers undergo phase separation with respect to their physico-chemical properties due to small temperature changes. Phase separation upon heating is characterized as a lower critical solution temperature (LCST) (Zhang, Q et al., Materials Horizons 2017, 4 (2), 109-116). In contrast, a polymer, which exhibits an upper critical solution temperature (UCST), phase separation, takes place upon cooling (Seuring, J. et al., Macromolecular Chemistry and Physics 2010, 211 (19), 2109-2117; Seuring, J. et al., Biomacromolecules 2011, 12 (10), 3418-3422; Meiswinkel, G. et al., Macromolecular rapid communications 2013, 34 (12), 1026-1031). Exemplarily, Seuring et al. reported and characterized the UCST type phase separation properties of a nonionic homopolymer poly(N-acryloyl glycinamide) in pure water (Seuring, J. et al., Macromolecules 2012, 45 (1), 374-384). In some rare cases, the phase separation leads to hydrogel formation, instead of precipitation. Over the last decades, most described systems in literature are based on synthetic or natural water-soluble polymers exhibiting lower critical solution temperature (LCST)-type thermosensitive gelation (Plunkett, K. N. et al., Langmuir 2006, 22 (9), 4259-4266; Gupta, N. R. et al., Carbohydrate Polymers 2015, 117, 331-338; Karakasyan, C. et al., Macromolecules 2001, 34 (14), 4958-4964; Koonar, I. et al., Langmuir 2012, 28 (51), 17785-17794; Taribagil, R. R. et al., Macromolecules 2010, 43 (12), 5396-5404). Only less a few examples can be found in literature were the gelation occurred via cooling the sample below a critical temperature (UCST). Particularly prominent examples are natural biopolymers like gelatin and pectin/chitosan-systems (Djabourov, M.; Leblond, J.; Papon, P., Gelation of Aqueous Gelatin Solutions. li Rheology of the Sol-Gel Transition, (http://dxdoiorg/101051/jphys:01988004902033300) 1988, 49; Birch, N. P. et al., Biomacromolecules 2015, 16 (6), 1837-1843). In the last years the interest in biofabrication, especially for tissue engineering and regenerative medicine has been rapidly growing developing into a promising interdisciplinary research field in its own right (Groll, J. et al., Biofabrication 2016, 8 (1), 013001). One major additive manufacturing technique used in the field is direct-ink writing of bioinks (Groll, J. et al., Biofabrication 2018, 11 (1), 013001). Often a hydrogel formulation, which enables printability and cell survival during the printing process is used (Chimene, D. et al., Hydrogel Bioink Reinforcement for Additive Manufacturing: A Focused Review of Emerging Strategies, Advanced Materials, 2020, 32 (1), 1902026). To date, most commonly hydrogels are based on natural biopolymers, such as gelatin, alginate and hyaluronic acid are used due to their generally good cytocompatibility (Valot, L. et al., Chemical Society Reviews 2019, 48 (15), 4049-4086). However, such systems based on biopolymers can also have limitations such as less-than-ideal printability and often considerable batch-to-batch variations, especially with respect to the rheological properties. The synthetic polymer platform formed by cyclic imino ethers, in particular poly (2-substituted-2-oxazoline)s (POx) and poly(2-substituted-5,6-dihydro-4H-1,3-oxazine)s (poly(2-oxazine)s, POzi), was investigated for decades as biomaterials in different applications due to good cytocompatibility and chemical versatility (Glassner, M. et al., Polymer International 2018, 67 (1), 32-45; Lorson, T. et al., Biomaterials 2018, 178, 204-280; Luxenhofer, R. et al., Macromolecular Bioscience 2018, 18 (6), 1800070). POx/POzi based systems were investigated as thermoresponsive materials (Dargaville, T. R. et al., Macromolecular Bioscience 2018, 18 (6), 1800070), biomedical applications (Harris, J. M. et al., European Polymer Journal 2019, 120, 109241; Moreadith, R. W. et al., European Polymer Journal 2017, 88, 524-552) and drug delivery (Sedlacek, O.; Hoogenboom, R., Drug Delivery Systems Based on Poly(2-Oxazoline)s and Poly(2-Oxazine)s, Advanced Therapeutics, 2020, 3 (1), 1900168) approaches. However, surprisingly few reports can be found that showed thermogelation in water of pure POx/POzi structures. In 2017 Lorson et al. established a LCST-type cytocompatible and printable supramolecular hydrogel based on POx/POzi diblock copolymers (Lorson, T. et al., Biomacromolecules 2017, 18 (7), 2161-2171). The system comprised a hydrophilic poly(2-methyl-2-oxazoline) block and a thermoresponsive poly(2-n-propyl-2-oxazine) block of similar block length. Another LCST-type hydrogel was described by Hoogenboom and Monnery (Monnery, B. D. et al., Polymer Chemistry 2019, 10 (25), 3480-3487). An BAB triblock copolymer bearing poly(2-n-propyl-2-oxazoline) (B) and hydrophilic poly(2-ethyl-2-oxazoline) blocks (A) showed sol/gel transitions upon heating, but extremely high degrees of polymerization were required. In 2019, Lübtow, Mrlik et al. described a different, much shorter ABA triblock copolymer, which forms stable, but relatively weak and barely printable, LCST-type hydrogels (Lubtow, M. et al., Temperature-Dependent Rheological and Viscoelastic Investigation of a Poly(2-Methyl-2-Oxazoline)-B-Poly(2-Iso-Butyl-2-Oxazoline)-B-Poly(2-Methyl-2-Oxazoline)-Based thermogelling Hydrogel, Journal of Functional Biomaterials, 2019, 10 (3), 36). Recently, the first UCST-type hydrogel formed by pure POx/POzi based block copolymers was described (L. Hahn et al., Inverse Thermogelation of Aqueous Triblock Copolymer Solutions into Macroporous Shear-Thinning 3D Printable Inks ACS Appl. Mater. Interfaces 2020, 12, 11, 12445-12456) Here, the ABA triblock copolymer comprising the hydrophilic poly(2-methyl-oxazoline) (PMeOx) and the aromatic hydrophobic poly(2-phenyl-2-oxazine) (PPheOzi) blocks undergoes unique gelation at lower temperatures. For block copolymers of PMeOx with poly(2-phenyl-2-oxazoline) (PPheOx), poly(2-benzyl-2-oxazine) (PBzOzi) and of PMeOx with poly(2-benzyl-2-oxazoline), gel formation was not observed in a comparable temperature range. The PMeOx/PPheOzi copolymer formed a stable hydrogel by entangled self-assembled worm-like micelles, which form from spherical micelles upon cooling. The limiting factor for using this system as a component in a bioink formulation was the gelation kinetics. Upon cooling, it takes about one hour to form a hydrogel suitable for printing. Shorter gelation times would be advantageous if viable cells are to be embedded.

Here, a new block copolymer is described and characterized for further usage e.g. as bioink component, which features the aromatic poly(2-phenethyl-2-oxazoline), and which undergoes inverse thermogelation in aqueous solution with pronounced and fast thermoresponsive sol/gel transition.

The following items provide a summary of the invention and its preferred embodiments.

1. A block copolymer (also referred to herein as the copolymer or the block copolymer of the present invention) comprising a polymer block (A) comprising repeating units of formula (I):

(I)

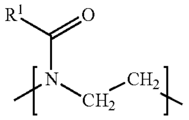

wherein $R^1$ is methyl or ethyl, and a polymer block (B) comprising repeating units of formula (II):

(II)

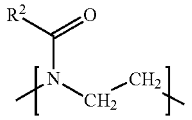

wherein $R^2$ represents a group —$CH_2$—$CH_2$-phenyl.

2. The block copolymer in accordance with item 1, wherein $R^1$ is methyl.
3. The block copolymer in accordance with item 1 or 2, wherein the number of repeating units of formula (I) in each polymer block (A) is, independently for each polymer block (A) if more than one polymer block (A) is present, 5 or more and 100 or less, more preferably 10 or more and 70 or less.
4. The block copolymer in accordance with item 3, wherein the number of repeating units of formula (I) in each polymer block (A) is, independently for each polymer block (A) if more than one polymer block (A) is present, 20 or more and 50 or less.
5. The block copolymer in accordance with item 4, wherein the number of repeating units of formula (I) in each polymer block (A) is, independently for each polymer block (A) if more than one polymer block (A) is present, 30 or more and 40 or less.
6. The block copolymer in accordance with item 1 or item 2, wherein the structure of the polymer block (A) is represented by formula (Ia):

(Ia)

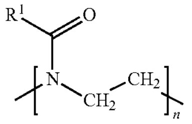

wherein $R^1$ is as defined in item 1 or 2, and n is 5 or more and 100 or less, more preferably 10 or more and 70 or less.

7. The block copolymer in accordance with item 6, wherein n is 20 or more and 50 or less.
8. The block copolymer in accordance with item 7, wherein n is 30 or more and 40 or less.
9. The block copolymer in accordance with any of items 1 to 8, wherein, if more than one polymer block (A) is present, the difference between the number of repeating units of formula (I) in the polymer block (A) with the highest number of repeating units of formula (I) and the polymer block (A) with the lowest number of repeating units of formula (I) among all polymer blocks (A) is not higher than 5, more preferably not higher than 2, and most preferably not higher than 1.
10. The block copolymer in accordance with any of items 1 to 9, wherein the number of repeating units of formula (II) in each polymer block (B) is, independently for each polymer block (B) if more than one polymer block (B) is present, 5 or more and 100 or less, more preferably 5 or more and 70 or less.
11. The block copolymer in accordance with item 10, wherein the number of repeating units of formula (II) in each polymer block (B) is, independently for each polymer block (B) if more than one polymer block (B) is present, 10 or more and 30 or less.
12. The block copolymer in accordance with item 11, wherein the number of repeating units of formula (II) in each polymer block (B) is, independently for each polymer block (B) if more than one polymer block (B) is present, is 10 or more and 20 or less.
13. The block copolymer in accordance with any of items 1 to 12, wherein the structure of the polymer block (B) is represented by formula (IIa):

(IIa)

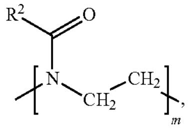

wherein m is 5 or more and 100 or less, more preferably 5 or more and 70 or less, and wherein $R^2$ is as defined in item 1.

14. The block copolymer in accordance with item 13, wherein m is 10 or more and 30 or less.
15. The block copolymer in accordance with item 14, wherein m is 10 or more and 20 or less.
16. The block copolymer in accordance with any of items 1 to 15, wherein the ratio of the total number of repeating units of formula (I) in the polymer block(s) (A) to the total number of repeating units of formula (II) in the polymer block(s) (B) in terms of the numbers of repeating units, is in the range of 20:1 to 1:1, more preferably 16:1 to 2:1.
17. The block copolymer in accordance with item 16, wherein the ratio of the total number of repeating units of formula (I) in the polymer block(s) (A) to the total number of repeating units of formula (II) in the polymer block(s) (B) in terms of the numbers of repeating units, is in the range of 8:1 to 3:1.
18. The block copolymer in accordance item 17, wherein the ratio of the total number of repeating units of formula (I) in the polymer block(s) (A) to the total number of repeating units of formula (II) in the polymer block(s) (B) in terms of the numbers of repeating units, is in the range of 5:1 to 4:1.
19. The block copolymer in accordance with any of items 1 to 18, wherein the degree of polymerization of the block copolymer is in the range of 40 to 180.
20. The block copolymer in accordance with item 19, wherein the degree of polymerization is in the range of 60 to 110.
21. The block copolymer in accordance with item 20, wherein the degree of polymerization is in the range of 80 to 100.
22. The block copolymer in accordance with any of items 1 to 21, which is a di- or triblock copolymer.

23. The block copolymer in accordance with any of items 1 to 22, which is a triblock copolymer of two polymer blocks (A) and one polymer block (B) having the structure (A)-(B)-(A).
24. The block copolymer in accordance with any of items 1 to 23, wherein the block copolymer is a triblock copolymer having the following copolymer structure (III):

(III)

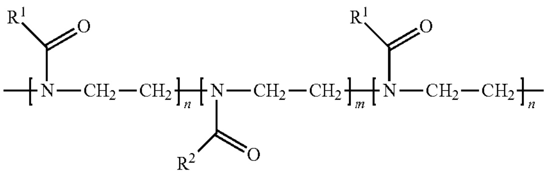

wherein $R^1$, $R^2$, n, independently for each occurrence, and m are defined as in the preceding items.
25. The block copolymer in accordance with item 24, wherein $R^1$ is methyl, $R^2$ is —$CH_2$—$CH_2$-phenyl, n is, independently for each occurrence, 30 or more and 40 or less, and m is 10 or more and 20 or less.
26. A hydrogel composition comprising the block copolymer in accordance with any of items 1 to 25.
27. The hydrogel composition in accordance with item 26, which comprises the block copolymer in accordance with any of items 1 to 25 at a concentration of 5 wt % or more and 30 wt % or less, based on the total weight of the hydrogel composition.
28. The hydrogel composition in accordance with item 27, which comprises the block copolymer in accordance with any of items 1 to 25 at a concentration of 10 wt % or more and 25 wt % or less, based on the total weight of the hydrogel composition.
29. The hydrogel composition in accordance with item 28, which comprises the block copolymer in accordance with any of items 1 to 25 at a concentration of 20 wt % or more and 25 wt % or less, based on the total weight of the hydrogel composition.
30. The hydrogel composition in accordance with any of items 26 to 29, which comprises the block copolymer in accordance with any of items 1 to 25 in combination with one or more further hydrogel forming polymer(s).
31. The hydrogel composition in accordance with item 30, wherein the one or more further hydrogel forming polymer(s) is (are) selected from alginate, gelatin, silk protein, collagen, fibrin and cellulose, or its derivatives.
32. The hydrogel composition in accordance with item 30 or 31, which comprises the one or more further hydrogel forming polymer(s) at a concentration of 0.1 to 4 wt %, preferably 1 to 2 wt %.
33. The hydrogel composition in accordance with any of items 26 to 32, wherein the weight ratio of the block copolymer in accordance with any of items 1 to 25 to the further hydrogel forming polymer(s) is in the range of 2:1 to 100:1, preferably 5:1 to 50:1, more preferably 10:1 to 25:1.
34. The hydrogel composition in accordance with any of items 26 to 33, which further comprises viable cells.
35. A method for the formation of a hydrogel composition in accordance with any of items 26 to 34, comprising the step of exposing an aqueous solution comprising the block copolymer in accordance with any of items 1 to 25 to a temperature of less than 25° C.
36. The method in accordance with item 35, wherein the aqueous solution comprising the block copolymer is exposed to a temperature of 20° C. or less.
37. The method in accordance with item 35 or 36, wherein the aqueous solution comprising the block copolymer is exposed to a temperature of not lower than 0° C.
38. Use of the block copolymer in accordance with any of items 1 to 25 or of the hydrogel composition in accordance with any of items 26 to 34 as a support material or a structural material in 3D printing.
39. Use of the block copolymer in accordance with any of items 1 to 25 or of the hydrogel composition in accordance with any of items 26 to 34 as an internal sacrificial support material in 3D printing.
40. Use of a hydrogel composition in accordance with any of items 26 to 34, preferably in accordance with item 34, as a bioink.
41. A method for the provision of a hydrogel scaffold with a predetermined geometry, comprising a step of subjecting a composition comprising the block copolymer in accordance with any of items 1 to 25, preferably the hydrogel composition in accordance with any of items 26 to 34, to 3D printing.
42. A method for the provision of an artificial tissue, comprising a step of forming a hydrogel scaffold comprising viable cells from the hydrogel composition in accordance with item 34.
43. The method of item 42, wherein the step of forming the hydrogel scaffold comprises 3D printing of the hydrogel composition in accordance with item 34.

In the context of the invention, it has been found that the specific combination of hydrophilic and hydrophobic aromatic moieties in the copolymer of the present invention allows a rapid thermoresponsive inverse gelation of the copolymer to be achieved, yielding a macroporous hydrogel. This hydrogel exhibited pronounced viscoelastic solid-like properties, as well as shear thinning, rapid structure recovery and good strain resistance properties. Excellent 3D-printability of the cytocompatible hydrogel at lower temperature opens a wide range of different applications in the field of biofabrication. For example, the hydrogel can be used as printing support or bioink, and further as a sacrificial bioink due to rapid dissolution at physiological conditions.

The block copolymer of the present invention comprises a polymer block (A) which comprises repeating units of formula (I):

(I)

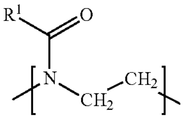

wherein $R^1$ is methyl or ethyl, preferably methyl.

In line with conventional practice, it will be understood that the brackets [ ] in formula (I) indicate that the entity within the brackets (i.e. —$N(C(O)R^1)$—$CH_2$—$CH_2$—) represents a repeating unit of the polymer block, and the lines crossing the brackets indicate the bonds which link the repeating unit to adjacent atoms or entities, typically to an adjacent repeating unit of the same polymer block, to an adjacent repeating unit of a different polymer block, or to a terminal group of the block copolymer. In addition to the repeating units of formula (I), the polymer block(s) (A) may comprise repeating units other than repeating units of formula (I). However, in order for the repeating units of formula (I) to provide the desired properties, the amount of repeating units other than the repeating units of formula (I) is typically limited e.g. to a maximum of 15 mol %, preferably a maximum of 10 mol % and more preferably a maximum of 5 mol %, based on the total number of repeating units in the concerned polymer block. Most preferably, all of the repeating units of the polymer block(s) (A) are repeating units of formula (I), i.e. the polymer block(s) (A) consist of repeating units of formula (I). Examples of repeating units other than repeating units of formula (I) are repeating units of the formula —$N(C(O)R^A)$—$CH_2$—$CH_2$, wherein $R^A$ is selected from alkyl other than methyl or ethyl, e.g. C3 to C6 alkyl, aryl, e.g. phenyl, aralkyl, e.g.—$CH_2$-phenyl, C2 to C6 alkenyl, C2 to C6 alkynyl, and functionalized alkyl, e.g. C1-C6 alkyl carrying a substituent selected from furanyl, maleimidyl, an azide, a carboxylic acid group and an amino group.

Preferably, $R^1$ is the same for all repeating units of formula (I) within each polymer block (A). If more than one polymer block (A) is present, it is preferred that all the polymer blocks (A) comprise the same repeating unit of formula (I).

The number of repeating units of formula (I) in each polymer block (A) is, independently for each polymer block (A) if more than one polymer block (A) is present, preferably 5 or more and 100 or less, more preferably 10 or more and 70 or less, still more preferably 20 or more and 50 or less, and even more preferably 30 or more and 40 or less, such as 34, 35, 36 or 37.

In line with the above, a preferred structure of the polymer block(s) (A) is indicated by the following formula (Ia):

(Ia)

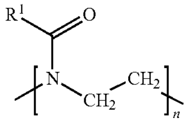

wherein $R^1$ is methyl or ethyl, more preferably methyl, and n is of 5 or more and 100 or less, more preferably 10 or more and 70 or less, still more preferably 20 or more and 50 or less, and even more preferably 30 or more and 40 or less, such as 34, 35, 36 or 37.

The number of repeating units of the polymer blocks, and thus the value of n, can be conveniently determined by $^1$H-NMR, e.g. using $^1$H-NMR endgroup analysis. Where necessary, the determination can be carried out by carrying out the analysis prior to the formation of a further polymer block and after the formation of a further polymer block, and comparing the analytic results obtained.

If more than one of the polymer blocks (A) is present in the block copolymer in accordance with the invention, e.g. two polymer blocks, the difference between the number of repeating units of formula (I) in the polymer block (A) with the highest number of repeating units of formula (I) and the polymer block (A) with the lowest number of repeating units of formula (I) among all polymer blocks (A) is not higher than 10, more preferably not higher than 5. If more than one of the polymer blocks (A) is present in the block copolymer in accordance with the invention, it is particularly preferred that the polymer blocks (A) have the same number of repeating units of formula (I).

The polymer block(s) (B) comprised by the block copolymer in accordance with the present invention comprise repeating units of formula (II):

(II)

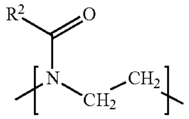

wherein $R^2$ represents a group —$CH_2$—$CH_2$-phenyl.

In line with conventional practice, it will be understood that the brackets [ ] in formula (I) indicate that the entity within the brackets (i.e. —$N(C(O)R^2)$—$CH_2$—$CH_2$—) represents a repeating unit of the polymer block, and the lines crossing the brackets indicate the bonds which link the repeating unit to adjacent atoms or entities, typically to an adjacent repeating unit of the same polymer block, to an adjacent repeating unit of a different polymer block, or to a terminal group of the block copolymer. In addition to the repeating units of formula (II), the polymer block(s) (B) may comprise repeating other than the repeating units of formula (II). However, in order for the repeating units of formula (II) to provide the desired properties, the amount of repeating units other than the repeating units of formula (II) is typically limited e.g. to a maximum of 15 mol %, preferably a maximum of 10 mol % and more preferably a maximum of 5 mol %, based on the total number of repeating units in the concerned polymer block. Most preferably, all of the repeating units of the polymer block(s) (B) are repeating units of formula (II), i.e. the polymer block(s) (B) consist of repeating units of formula (II). Examples of repeating units other than repeating units of formula (II) are repeating units of the formula —$N(C(O)R^B)$—$CH_2$—$CH_2$, wherein $R^B$ is selected from alkyl, e.g. C1 to C6 alkyl, aryl, e.g. phenyl, aralkyl other than-$CH_2$—$CH_2$-phenyl, e.g.—$CH_2$-phenyl, C2 to C6 alkenyl, C2 to C6 alkynyl, and functionalized alkyl, e.g. C1-C6 alkyl carrying a substituent selected from furanyl, maleimidyl, an azide, a carboxylic acid group and an amino group.

The number of repeating units of formula (II) in each polymer block (B) is, independently for each polymer block (B) if more than one polymer block (B) is present, preferably 5 or more and 100 or less, more preferably 5 or more and 70 or less, still more preferably 10 or more and 30 or less, and even more preferably 10 or more and 20 or less, such as 14, 15, 16 or 17.

In line with the above, a preferred structure of the polymer block(s) (B) is indicated by the following formula (IIa):

(IIa)

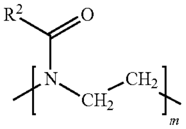

wherein $R^2$ is-$CH_2$—$CH_2$-phenyl, and m is 5 or more and 100 or less, more preferably 5 or more and 70 or less, still more preferably 10 or more and 30 or less, and even more preferably 10 or more and 20 or less, such as 14, 15, 16 or 17.

The number of repeating units of a polymer block, and thus the value of m, can be conveniently determined by $^1$H-NMR, e.g. using $^1$H-NMR endgroup analysis. Where necessary, the determination can be carried out by carrying out the analysis prior to the formation of a further polymer block and after the formation of a further polymer block, and comparing the analytic results obtained.

If more than one of the polymer blocks (B) is present in the block copolymer in accordance with the invention, e.g. two polymer blocks, the difference between the number of repeating units of formula (II) in the polymer block (B) with the highest number of repeating units of formula (II) and the polymer block (B) with the lowest number of repeating units of formula (I) among all polymer blocks (B) is not higher than 10, more preferably not higher than 5. However, it is particularly preferred that the block copolymer of the present invention comprises one polymer block (B).

The ratio of the total number of repeating units of formula (I) forming the polymer block(s) (A) to the total number of repeating units of formula (II) forming the polymer block(s) (B) in any block copolymer in accordance with the invention, in terms of the numbers of repeating units, is preferably in the range of 20:1 to 1:1, more preferably 16:1 to 2:1, still more preferably 8:1 to 3:1, and even more preferably 5:1 to 4:1. This ratio can be determined, e.g., by measuring the relative amounts of side chains $R^1$ and phenyl side chains via $^1$H-NMR analysis and calculating their ratio accordingly.

The degree of polymerization of the block copolymer in accordance with the present invention, indicated as an average value (number average) of the total number of repeating units in the block copolymer, is preferably in the range of 40 to 180, more preferably in the range of 60 to 110, and still more preferably 80 to 100. It can be determined, e.g., via $^1$H-NMR endgroup analysis.

The term "block copolymer" is used herein in accordance with its established meaning in the art to refer to copolymers wherein repeating units of a defined type are organized in blocks. Typically, the block (A) or blocks (A) contained in the block copolymer in accordance with the invention can be considered as polymers themselves, and the same applies for the block (B) or the blocks (B). The polymer providing a polymer block may be a homopolymer or a copolymer, and is preferably a homopolymer. Thus, reference may be made herein to a "polymer A" providing the polymer block(s) (A), and to a "polymer B" providing the polymer block(s) (B) in the copolymer in accordance with the invention.

The block copolymer according to the invention comprises a polymer block (A) and a polymer block (B) as defined herein. It can comprise other repeating units and/or other polymer blocks in addition to the polymer block(s) (A) and the polymer block(s) (B). However, preferably all of the repeating units contained in the block copolymer are either repeating units of formula (I) forming the polymer block(s) (A) or repeating units of formula (II) forming the polymer block(s) (B) as defined above. Thus, preferably, the polymeric entities of the block copolymer consist of one or more polymer block(s) (A) and one or more polymer block(s) (B). It will be understood that such a block copolymer, wherein the polymeric entities consist of one or more polymer block(s) (A) and one or more polymer block(s) (B), can comprise, in addition to the polymer blocks (A) and (B), groups which are not repeating units, e.g. a terminal group such as a hydrogen atom, a methyl group, a propargyl group, a tert-butyl piperazinyl-1-carboxylate (1-Boc-piperazinyl) group or an ethyl isonipectoate (EIP) group. Such a terminal group may originate, e.g., from a polymerization initiator or from a terminating agent.

The block copolymer in accordance with the present invention typically has a structure selected from a linear block copolymer, a star-like block copolymer, and a block copolymer with a graft structure or a brush copolymer. Preferred is a linear block copolymer. As will be understood by the skilled reader, in such a linear structure, there are either two polymer blocks (A)-(B) or (B)-(A), three polymer blocks (A)-(B)-(A) or (B)-(A)-(B), or more polymer blocks (A) and (B) linearly arranged in an alternating fashion. Among these linear block copolymers, preference is given to a diblock copolymer (A)-(B) or (B)-(A), and to a triblock copolymer (A)-(B)-(A). Most preferred as the block copolymer in accordance with the invention is a triblock copolymer having the structure (A)-(B)-(A), i.e. a triblock copolymer comprising two polymer blocks (A) and one polymer block (B) in the order of (A)-(B)-(A).

As apparent from the above, a strongly preferred block copolymer in accordance with the invention is an (A)-(B)-(A) triblock copolymer having the following structure (III):

(III)

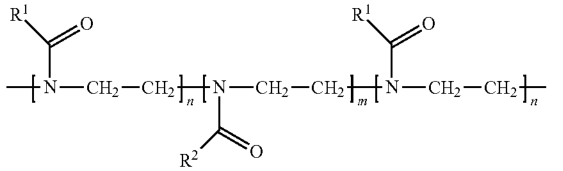

wherein $R^1$, $R^2$, n, independently for each occurrence, and m are defined as above, including any preferred embodiments of these variables.

In line with conventional practice, formula (III) shows that the polymeric entities of the block copolymer of formula (III) consists of the three polymer blocks, the first one being formed by n repeating units of the formula $—N(C(O)R^1)—CH_2—CH_2—$, the second one being formed by m repeating units of the formula $—N(C(O)R^2)—CH_2—CH_2—$, and the third one being formed by n repeating units of the formula $—N(C(O)R^1)—CH_2—CH_2—$.

As will be understood by the skilled person, the open bonds at the polymer terminals on the left side and on the right side of formula (III) will typically be attached to groups which are not repeating units, i.e. terminal groups of the block copolymer, such as a hydrogen atom, a methyl group, a propargyl group, a tert-butyl piperazinyl-1-carboxylate (1-Boc-piperazinyl) group or a ethyl isonipectoate (EIP) group. Such a terminal group may originate, e.g., from a polymerization initiator or from a terminating agent.

Further in line with the above, it is particularly preferred also for formula (III) that $R^1$ is methyl, n is, independently of each occurrence, 20 or more and 50 or less, and even more preferably 30 or more and 40 or less; m is 10 or more and 30 or less, and even more preferably 10 or more and 20 or less; and that the degree of polymerization is 60 to 110, and even more preferably 80 to 100.

The block copolymers of the present invention can be prepared by polymerization methods known in the art, the polymer synthesis is well reproducible and scalable. For example, the block copolymers in accordance with the present invention can be conveniently prepared via cationic ring-opening polymerization of 2-substitutet 2-oxazolines. Thus, the copolymers are also referred to as poly(2-oxazolines).

Suitable 2-substituted 2-oxazolines of the following formula, which carry a methyl or ethyl group or which carry a phenethyl group $—CH_2—CH_2$-phenyl as a substituent are available as described by Witte and Seeliger (Witte, H.; Seeliger, W., Simple Synthesis of 2-Substituted 2-Oxazolines and 5,6-Dihydro-4h-1,3-Oxazines. Angewandte Chemie International Edition in English 1972, 11 (4), 287-288). Suitable conditions for the cationic ring opening polymerization of 2-substituted 2-oxazoline monomers are discussed, e.g., by R. Luxenhofer and R. Jordan, Macromolecules 39, 3509-3516 (2006), T. Bonné et al., Colloid. Polym. Sci., 282, 833-843 (2004), T. Bonne et al., Macromol. Chem. Phys. 2008, 1402-1408, (2007), or L. Hahn et al., Biomacromolecules 2018, 19, 7, 3119-3128; Lübtow, M. M.; et al., JACS 2017, 139 (32), 10980-10983).

As will be understood by the skilled person, the molar mass or degree of polymerization of the block copolymer in accordance with the invention can be controlled, e.g., by controlling the ratio of the amount of a polymerization initiator to the amount of monomers.

It has been found that the block copolymers in accordance with the invention are able to form a hydrogel, and that the formation of this hydrogel is reversible. Thus, as a further aspect, a hydrogel composition is provided which comprises a block copolymer of the present invention. As implied by the term hydrogel, the hydrogel composition comprises the block copolymer in accordance with the invention and water or an aqueous medium suitable for cell culture, in a gelled state. The hydrogel composition may consist of the block copolymer of the present invention and water or an aqueous medium suitable for cell culture, or may contain one or more further components, for which examples shall be given below. In the hydrogel composition, the block copolymer in accordance with the invention forms a network wherein water or the aqueous medium is contained. Without wishing to be bound by theory, it is assumed that the macromolecules of the block copolymer form a network via non-covalent interactions of their polymer chains or of blocks contained therein, respectively. It will be further understood that the hydrogel can comprise one or more types of the block copolymer in accordance with the invention. If more than one type of such a copolymer is used, the types of block copolymer may differ, e.g., with respect to the degree of polymerization of one or more of the polymer blocks contained therein.

The hydrogel composition in accordance with the invention preferably comprises the block copolymer in accordance with the invention at a concentration of 5 wt % or more, preferably 10 wt % or more, more preferably 20 wt % or more, based on the total weight of the hydrogel composition. The concentration of the block copolymer in the composition is typically 40 wt % or less, preferably 30 wt % or less, and more preferably 25 wt % or less, based on the total weight of the hydrogel composition.

As noted above, the hydrogel composition in accordance with the invention may comprise further components in addition to the block copolymer in accordance with the invention and water.

For example, the hydrogel composition may comprise the block copolymer in accordance with the invention in combination with one or more further hydrogel forming polymer (s). Such further hydrogel forming polymers are preferably biopolymers, and include, for example, proteins or polysaccharides. As will be understood by the skilled person, a hydrogel forming polymer is a polymer which is suitable to form a polymer network in a hydrogel, either as such or assisted by a crosslinking agent. Crosslinking of the polymer to provide a hydrogel may be accomplished by covalent bonds, physical interactions or by other attractive forces between polymer molecules, e.g. ionic interactions. In the hydrogel composition in accordance with the invention, the further hydrogel forming polymer may be present in a crosslinked state, or in a state which still allows the crosslinking to be accomplished in order to further support the hydrogel provided by the block copolymer in accordance with the invention. As preferred examples of a further hydrogel component, mention may be made of alginate, gelatin, silk protein, collagen, fibrin, or cellulose, or its derivatives.

Typical concentrations of the one or more further hydrogel forming polymer(s), if present, range from 0.1 to 4 wt %, preferably 1 to 2 wt %, based on the total weight of the hydrogel composition, and are indicated as the total concentration if more than one further hydrogel forming polymer is present.

If one or more further hydrogel forming polymer(s) is (are) present, the weight ratio of the block copolymer in accordance with the invention to the further hydrogel component(s) is preferably in the range of 2:1 to 100:1, more preferably 5:1 to 50:1, and still more preferably 10:1 to 25:1.

Another example of a further component which may be present in the hydrogel composition in accordance the invention together with the block copolymer in accordance with the invention are viable cells. A hydrogel composition in accordance with the invention comprising viable cells preferably also comprises one or more further hydrogel forming polymer(s) as discussed above. Moreover, the water in a hydrogel composition comprising viable cells will typically be present in an aqueous medium suitable for cell culture which may comprise e.g. salts and/or a buffer.

As explained above, the block copolymers of the present invention are thermoresponsive, i.e. they are able to form a hydrogel in reaction to a temperature stimulus, in particular in reaction to an exposure to a temperature below a certain level.

Thus, the hydrogel composition in accordance with the invention can be conveniently formed using an aqueous solution comprising the block copolymer in accordance with the invention. Preferred concentrations of the block copolymer, and of other optional and preferred components of the hydrogel composition are as discussed above for the hydrogel composition. As will be understood by the skilled reader, an aqueous solution is a solution comprising water as a solvent, typically as a main solvent in an amount of 50 wt % or more (based on the total weight of solvent as 100%), preferably in an amount of 75 wt % or more and more preferably in an amount of 90 wt % or more. Most preferably, the aqueous solution uses water as the only solvent.

In order to provide such a solution, the block copolymer can be dissolved in an appropriate amount of water or of an aqueous medium for cell culture. As will be understood by the skilled person, the solution is preferably prepared using an aqueous solvent or a mixture of the aqueous solvent and the block copolymer with a temperature at or above the temperature where the hydrogel formed by the block copolymer in accordance with the invention liquefies, e.g. at or above a temperature of 25° C.

In order to allow the formation of a hydrogel, it is sufficient to expose the aqueous solution comprising the block copolymer to a temperature which allows the gelation to proceed, i.e. a temperature that lies below the temperature at which the hydrogel liquefies. This may involve cooling of the aqueous solution. Thus, a further aspect of the present invention relates to a method for the formation of a hydrogel, comprising the step of cooling an aqueous solution comprising a block copolymer in accordance with the invention. Typically, the aqueous solution is exposed for this purpose to a temperature of less than 25° C. In order to accelerate the formation of the gel, it is preferred to expose the aqueous solution to a temperature of 22° C. or less, more preferably 15° C. or less, e.g. 5 to 10° C. The temperature to which the solution is exposed to allow the formation of the hydrogel is typically not lower than 0° C.

Once the hydrogel has formed, it remains stable until it is exposed to a temperature which is sufficiently high to turn the hydrogel into a liquid, e.g. a temperature of 25° C. The process of gelation and dissolution of the hydrogel below and above the temperature for hydrogel formation, respectively, can be repeated without limitations.

Since the temperature for liquefaction of the hydrogel comprising the block copolymer in accordance with the present invention lies well below a temperature where the viability of cells is affected, the block copolymer or the hydrogel composition are suitable as a matrix for the incorporation and the release of viable cells. Moreover, since the temperature lies below body temperature, the block copolymer or the hydrogel composition can be used for providing a scaffold structure with a predetermined geometry (referred to herein as "hydrogel scaffold"), inserting the hydrogel scaffold into the body, and allowing it to liquefy by exposing it to body temperature. This can be a useful approach to release a material, such as biological cells, contained in the hydrogel scaffold. Another related application is the use of the hydrogel as a sacrificial material in a composite scaffold structure comprising a material which remains solid at the temperature at which the hydrogel in accordance with the invention is liquefied in combination with the hydrogel in accordance with the invention. Once the composite scaffold structure is exposed to a temperature at which the hydrogel in accordance with the invention is liquefied, e.g. body temperature, the parts of the scaffold structure provided by the hydrogel as a sacrificial material dissolve, leaving behind defined empty spaces, e.g. channels, in the structure.

Due to its physico-chemical characteristics shown herein, the block copolymer in accordance with the invention or a hydrogel composition comprising it can be beneficially processed by 3D printing to provide a hydrogel scaffold with a predetermined geometry. For this purpose, e.g. an extrusion-based printer can be used which extrudes a hydrogel composition in accordance with the invention through a nozzle while keeping the composition at or below the temperature at which the block copolymer forms a hydrogel. Using this approach, the hydrogel provided by the block copolymer in accordance with the invention can form a matrix which incorporates viable cells, and which allows the cells to be arranged in a predetermined shape, e.g. for the formation of artificial tissue. Likewise, the hydrogel provided by the block copolymer in accordance with the invention may provide the required stability during and immediately after 3D printing in a hydrogel composition comprising a further hydrogel forming polymer which, as such, cannot be conveniently 3D printed with good shape fidelity by itself, such as the further hydrogel forming polymers discussed above, e.g. alginate. Depending on the type of further hydrogel forming polymer used, it may be a useful approach to subject the hydrogel composition in accordance with the invention to 3D printing while the further hydrogel forming polymer is not crosslinked, and to subject the further hydrogel forming polymer to crosslinking after the 3D printing step.

In line with the above, a further aspect of the invention relates to the use of the block copolymer or the hydrogel composition in accordance with the invention for 3D printing, e.g. as a support material, as a structural material, or as a sacrificial material. For use as a sacrificial material in 3D printing, it is preferred to use a hydrogel composition consisting of the block copolymer in accordance with the invention and water, so that the hydrogel can be conveniently dissolved after printing. As noted above, it is preferred for 3D printing applications of the hydrogel composition in accordance with the invention that 3D printing is carried out at or below the temperature at which the block copolymer in accordance with the invention forms a hydrogel.

A related aspect relates to the use of a composition comprising the block copolymer in accordance with the invention, preferably a hydrogel composition in accordance with the invention, as a bioink e.g. for the formation of artificial tissue via 3D printing. For bioink applications, a hydrogel composition in accordance with the invention is preferred which comprises, together with the block copolymer in accordance with the invention and water or an aqueous medium suitable for cell culture, a further polymer for hydrogel formation as discussed above and viable cells.

In another aspect, the invention relates to a method for the provision of a hydrogel scaffold with a predetermined geometry, said method comprising a step of subjecting a composition comprising the block copolymer in accordance with the invention, preferably the hydrogel composition in accordance with the invention, to 3D printing.

Still a further aspect of the invention is a method for the provision of an artificial tissue, which method comprises a step of forming a hydrogel scaffold comprising viable cells from a hydrogel composition in accordance with the invention comprising viable cells. Preferably, the step of forming the hydrogel scaffold comprises 3D printing of the hydrogel composition comprising viable cells. Also in the context of this aspect, the hydrogel composition in accordance with the invention is preferably one which comprises, together with the block copolymer in accordance with the invention and water, a further polymer for hydrogel formation as discussed above, preferably a biopolymer, and viable cells. Following the formation of the hydrogel scaffold, crosslinking of the further polymer for hydrogel formation may be accomplished if the further polymer is not yet crosslinked. Moreover, after the formation of the hydrogel scaffold, and optionally after the crosslinking of a further polymer for hydrogel formation, the hydrogel scaffold can be brought into contact with a cell culture medium. Following this approach, the hydrogel formed by the block copolymer in accordance with the invention can be dissolved in the cell culture medium, leaving behind a hydrogel scaffold formed by the further polymer for hydrogel formation, e.g. a biopolymer, and comprising viable cells.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

EXPERIMENTAL SECTION

Abbreviations

MeOx 2-methyl-2-oxazoline
PhenOx 2-phenethyl-2-oxazoline
PMeOx poly(2-methyl-2-oxazoline)

PPhenOx poly(2-phenethyl-2-oxazoline)

A-PPhenOx-A Block copolymer formed by two poly(2-methyl-2-oxazoline) blocks as blocks A, and a poly(2-phenethyl-2-oxazoline) block

General Information

All substances and reagents for the monomer synthesis and polymerization were purchased from Sigma-Aldrich (Steinheim, Germany) and TCI-chemicals (Eschborn, Germany) and were used as received without further purification unless otherwise stated. For polymerization all substances were refluxed over $CaH_2$ for several hours and distilled prior usage. The solvent benzonitrile (PhCN) was dried over phosphorus pentoxide.

Monomer Synthesis and Characterization

The monomer synthesis of 2-phenethyl-2-oxazoline was carried out as described by Witte and Seeliger (Witte, H.; Seeliger, W., Simple Synthesis of 2-Substituted 2-Oxazolines and 5,6-Dihydro-4h-1,3-Oxazines. Angewandte Chemie International Edition in English 1972, 11 (4), 287-288). For the reaction 1 eq of 3-phenylpropionitrile, 1.2 eq. of amino-ethanol and catalytic amounts of zinc acetate dihydrate were added to a argon flushed flask and heated to 130° C. under reflux for several days until the reaction mixture turned brown. Reaction progress was controlled by $^1$H-NMR-spectroscopy. After completion, the mixture was dissolved in dichloromethane and washed with $H_2O$ (three times). The organic phase was dried with $MgSO_4$ and concentrated. The raw product was refluxed with $CaH_2$ and purified via vacuum distillation under argon atmosphere to yield the product as a colorless liquid. The resulting compound 2-phenethyl-2-oxazoline was characterized via refractive index, GC-ESI-MS analysis, and 1H- and $^{13}$C-NMR spectroscopy.

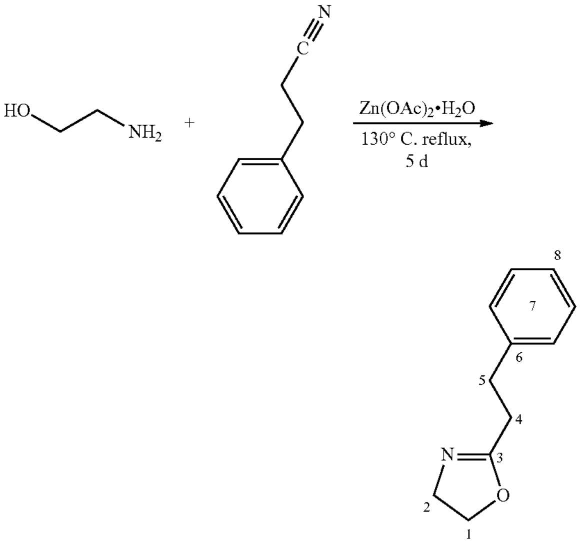

Yield: 9.0 g (51.4 mmol, 45.0%)

Boiling point: 65° C. (0.005 mbar)

$n_D^{20}$: 1.5510

EI-MS (m/z): theoretical: 175.10 $[C_{11}H_{13}NO]\cdot$ results: 175.1 $[C_{11}H_{13}NO]\cdot$, 98.1 $[C_5H_8NO]\cdot$; 91.1 $[C_7H_7]'\cdot$, 77.1 $[C_6H_5]\cdot$, 65.1 $[C_5H_5]\cdot$; 51.1 $[C_4H_3]\cdot$ $^1$H-NMR: ($CD_2Cl_2$, 300.12 MHz, 298 K): δ [ppm]=7.28-7.17 (m, 5H, $H^{7/8}$), 4.19 (t, 2H, $^3$J=9.4 Hz, $H^1$), 3.76 (t, 2H, $^3$J=9.4 Hz, $H^2$), 2.94 (t, 2H, $^3$J=7.9 Hz, $H^5$), 2.54 (t, 2H, $^3$J=7.9 Hz, $H^4$)

$^{13}$C-NMR: ($CD_2Cl_2$, 300.12 MHZ, 298 K): δ [ppm]=167.7 ($C^3$), 141.7 ($C^6$), 128.9 ($C^7$), 128.85 ($C^7$), 126.6 ($C^8$), 67.8 ($C^1$), 55.1 ($C^2$); 32.6 ($C^5$), 30.2 ($C^4$).

The refractive index of the synthesized monomer 2-phenethyl-2-oxazoline was determined on a RFM 870 refractometer from Bellingham+Stanley at 20° C. (Farnborough, England).

The monomer was further analyzed via mass-spectrometry using an Agilent 5977B MDS system coupled with a gas-chromatography system Agilent 7820A. The GC-system was equipped with an Agilent 19091S-433UI HP-5 ms ultra inert column (30 m×250 μm×0.25 μm). Temperature gradient was set from 40° C. to 300° C. with constant heat rate of 15° C./min and a constant flow of 1 mL/min.

Polymer Synthesis and Characterization

The block copolymer were synthesized following a general procedure based on previous reports (Hahn, L.; Lubtow, M. M.; Lorson, T.; Schmitt, F.; Appelt-Menzel, A.; Schobert, R.; Luxenhofer, R., Investigating the Influence of Aromatic Moieties on the Formulation of Hydrophobic Natural Products and Drugs in Poly(2-Oxazoline)-Based Amphiphiles. Biomacromolecules 2018, 19 (7), 3119-3128; Lübtow, M. M.; Hahn, L.; Haider, M. S.; Luxenhofer, R., Drug Specificity, Synergy and Antagonism in Ultrahigh Capacity Poly(2 -Oxazoline)/Poly(2-Oxazine) Based Formulations. Journal of the American Chemical Society 2017, 139 (32), 10980-10983).

Copolymer P1:

Under dry and inert conditions 93.0 mg (0.57 mmol, 1 eq) MeOTf and 1.70 g (20.0 mmol, 35 eq) of MeOx were added to 16 mL of dry PhCN and stirred for 3 hours at 110° C. After completion of the first block the mixture was cooled to room temperature and 1.50 g (8.54 mmol, 15 eq) of PhenOx was added. After stirring over night at 120° C., 1.70 g (20.0 mmol, 35 eq) of MeOx was added. The termination was carried out using 212 mg (1.14 mmol, 2 eq) N-Boc-piperazine at 45° C. The solvent was removed at reduced pressure. The residue was dissolved in deionized water, dialyzed overnight using a membrane with a MWCO of 1 kDa and freeze dried.

Yield: 4.64 g (0.49 mmol; 86.6%)

$M_{w,theor.}$: 8.8 kg/mol

GPC (HFIP): $M_n$=4.8 kg/mol; Đ=1.12

FIG. 1 shows the GPC-Traces after every block and the purified ABA-triblock copolymer P1.

$M_n$(1$^{st}$ block): 1.8 kg/mol, Đ(1$^{st}$ block): 1.05

$M_n$(2$^{nd}$ block): 2.9 kg/mol, Đ(2$^{nd}$ block): 1.08

FIG. 2 shows the $^1$H-NMR of the purified ABA-triblock copolymer Me-$PMeOx_{37}$-b-$PPhenox_{17}$-b-$PMeox_{36}$-PipBoc ($M_w$: 9.4 kg/mol, PMeOx/PPhenOx: 4.3) in $CD_3CN$.

Copolymer P2:

Under dry and inert conditions 193 mg (1.18 mmol, 1 eq.) MeOTf and 3.34 g (39.2 mmol, 33 eq.) of MeOx were added to 24 mL of dry PhCN and stirred for 3 hours at 110° C. After completion of the first block the mixture was cooled to room temperature and 3.01 g (17.1 mmol, 15 eq.) of PhenOx was added. After stirring over night at 120° C., 3.36 g (39.5 mmol, 33 eq.) of MeOx was added. The termination was carried out using 550 mg (3.5 mmol, 3 eq.) Ethylisonipecotate at 45° C. The solvent was removed at reduced pressure. The residue was dissolved in deionized water, dialyzed overnight using a membrane with a MWCO of 1 kDa and freeze dried.

Yield: 9.12 g (0.98 mmol; 83.1%)

$M_{w,theor.}$: 8.8 kg/mol

GPC (HFIP): $M_n$=4.3 kg/mol; d=1.17

GPC-Traces after every block and the purified ABA-triblock copolymer:

FIG. 3 shows the GPC-Traces after every block and the purified ABA-triblock copolymer P2.

$M_n$($1^{st}$ block): 2.3 kg/mol, Đ($1^{st}$ block): 1.08

$M_n$($2^{nd}$ block): 3.3 kg/mol, Đ($2^{nd}$ block): 1.12

FIG. 4 shows the $^1$H-NMR of purified ABA-triblock copolymer Me-$PMeOx_{36}$-b-$PPhenOx_{17}$-b-$PMeOx_{36}$-EIP (Mw: 9.3 kg/mol, PMeOx/PPhenOx: 4.1) in $CD_3CN$.

Nuclear magnetic resonance (NMR) was performed on a Bruker Fourier 300 (1H: 300.12 MHz) spectrometer at 298 K from Bruker BioSpin (Rheinstetten, Germany) and calibrated using the solvent signal.

Gel permeation chromatography (GPC) was performed on a Polymer Standard Service PSS (Mainz, Germany) system with following specifications: pump mod. 1260 infinity, MDS RI-detector mod. 1260 infinity (Agilent Technologies, Santa Clara, California, USA), precolumn: 50×8 mm PSS PFG linear M; 2 columns: 300×8 mm PSS PFG linear M (particle size 7 μm; pore size 0.1-1.000 kg/mol) with hexafluoroisopropanol (HFIP, containing 3 g/L potassium trifluoroacetate (KTFA)) as eluent calibrated against PEG standards with molar masses from 0.1 g/mol to 1000 kg/mol. The columns were held at 40° C. and the flow rate was set to 0.7 mL/min. Prior to each measurement, samples were dissolved in eluent and filtered through 0.2 μm PTFE filters (Rotilabo, Karlsruhe, Germany) to remove particles, if any.

Rolling ball viscosity experiments were performed on a LOVIS 2000M microviscometer from Anton Paar (Graz, Austria) using a LOVIS 1.8 capillary and a steel ball of 1.5 mm diameter. Prior to the viscosity measurements the density was determined at 5° C. and 40° C. using a DMA 4100 M density meter from Anton Paar (Graz, Austria). A temperature scan from 5° C.→40° C. and 40° C.→5° C. of a 10, 15 and 20 wt. % aqueous sample was performed to establish the temperature dependent dynamic viscosity.

Rheology investigations were recorded on an Anton Paar (Ostfildern, Germany) Physica MCR 301 system utilizing a plate-plate geometry (25 mm diameter) equipped with a solvent trap and Peltier element for temperature control. All aqueous samples were measured after complete dissolution in Millipore water and a concentration of 20 wt. % at 5° C. For investigations of viscoelastic behavior, the linear viscoelastic region (LVE) was determined by performing an amplitude sweep (0.02%→500%) strain deformation using a fixed angular frequency of 10 rad/s. Subsequently a frequency sweep (0.1 rad/s→500 rad/s) was performed at fixed strain deformation of 0.1%. For dispense plotting rheological preconditions of the hydrogel are shear-thinning properties, defined force resistance profile and fast structure-recovery after deformation. For steady shear experiments, the control shear rate mode was used (0.001 1/s→1000 1/s). The pronounced viscosity n decrease was fitted using the power-law expression $$\eta = K \cdot (\dot{\gamma})^{n-1}$$

where K is the consistency index, η the flow index and y the applied shear rate.

Using the steady stress sweep (5 Pa→1500 Pa) the onset value of viscosity decrease is refereed as yield point of the hydrogel system. To investigate the structure recovery properties, two different recovery testing experiments were performed. During the ORO-experiment (oscillation-rotational-oscillation) a low strain deformation of 0.5% is followed by a high shear rate of 100 1/s. In ROR-experiment (rotational-oscillation-rotational) a low shear rate region of 0.1 1/s is followed by a high strain of 100%.

For scanning electron microscopy of the native hydrogel structure, we investigated a cryogenic sample preparation procedure. For this, hydrogel samples were placed between two aluminium holders (d=3 mm), both containing a notch with a diameter of 2 mm, inclosing the sample and rapidly frozen in slush nitrogen (SN) at −210° C. The samples were then transferred into the sputter coater with a Leica EM VCT100 cryo-shuttle at −140° C. (Leica Microsystems ACE 400, Wetzlar, Germany). Here, the upper half of the sample was knocked off to create a fresh fractured surface and freeze-etched at −85° C. for 15 minutes under vacuum ($<1\cdot10^{-3}$ mbar). The samples were finally sputtered with 3 nm platinum and transferred with the cryo-shuttle into the SEM chamber. The morphology of the fractured surfaces was imaged at −140° C., by detecting SE using acceleration voltages of 2 kV or 8 kV.

To investigate the printability of 20 wt. % hydrogel samples, a compact bench-top 3D bioprinter (BioX, Cellink, Schweden) working on the principle of an extrusion-based printer was used. The printhead and the print bed were cooled to 8° C. prior to each printing process. The printing speed was set to 10 mm/s and a pressure of 120-160 kPa was applied (Nozzle: 25 G, stainless steel, length of 6.35 mm). First the printing resolution was investigated by increasing the strand-center to strand-center distance stepwise from 0.5 mm→0.75 mm→1 mm→1.5 mm→2 mm (Layer height 0.25 mm). To investigate the stiffness/steadiness of the hydrogel a strand collapse test was investigated like described by Ribeiro et al (Ribeiro, A.; Blokzijl, M. M.; Levato, R.; Visser, C. W.; Castilho, M.; Hennink, W. E.; Vermonden, T.; Malda, J., Assessing Bioink Shape Fidelity to Aid Material Development in 3d Bioprinting. Biofabrication 2017, 10 (1), 014102). The distance between the two edition points increased from 0.1→0.2→0.4→0.9→1.7 cm. Finally, real 3D printing was performed by printing a 20 layered tubular construct of 5 mm total height and 5 mm diameter using the parameters already described.

To evaluate the cytocompatibility of POx/Alginate (20:1 wt. %) bioinks, NIH3T3 cells (ATCC, Germany) were used (1 Mio/mL). As reference pure alginate solution (1 wt. %) was used. After homogenous cell distribution at 37° C. a simple one layered square structure (Figure S6) was printed at 10° C. using a 3D bioprinter BioX (Cellink, Sweden) and printing pressure of 50 kPa and printing speed of 5 mm/s. Stabilization after printing was performed using a 0.1 M $CaCl_2$) aqueous solution (10 minutes). The crosslinked scaffolds were incubated for 24 h at 37° C. in cell culture medium (DMEM high glucose (Gibco from Sigma Aldrich) and supplemented with 1% pen/strep, 2% glutamine (Thermo Fisher) and 10% bovine calf serum from Corning under controlled conditions (5% $CO_2$, 95% relative humidity). To assess the cell viability, printed NIH3T3-cells were stained insight the scaffolds using Calcein AM (Invitrogen, Thermo Fisher) after 24 h of cultivation, whereas blue nuclei acid stain (DAPI) (Thermo Fisher) was used to visualize nuclei of all embedded cells. ImageJ software was used to determine the cell viability using automatic cell counting in 3 fluorescence images (n=3) of 3 different samples (n=3) obtained with an epifluorescence microscope (Zeiss Observer, Germany) using the following equation:

$$\text{cell viability} = \frac{[\text{number of living cells}]}{[\text{number of cell nuclei}]}$$

Results and Discussion

Two batches of a block copolymer $PMeOX_{35}$-b-$PPhenOX_{15}$-b-$PMeOX_{35}$ were synthesized by living cationic ring opening polymerization (LCROP) and characterized by $^1$H-NMR spectroscopy and GPC. The successful termination using different terminating agents (P1: BOC-Pip, P2: EIP), the comparable degree of polymerization of approx. 90 repeating units as well as a ratio of PMeOx/PPhenOx of 4 was verified by corresponding signal intensities in $^1$H-NMR spectra. Via GPC, the number average molar mass $M_n$ and the dispersity Đ($M_w$/$M_n$) of both batches were compared after completion of every single block and purification of the final polymer product. Both batches show reasonably narrow molar mass size distributions (Đ(P1): 1.12, Đ(P2): 1.17) and an increase of the number average molar mass during the polymerization reaction, indicative of the living polymerization. A relevant structural difference between these novel polymers in comparison to previously described aromatic amphiphiles is the ethanediyl linker for the phenyl group in the repeat units in the block B, which leads to significantly altered physico-chemical properties.

When the concentration exceeded 20 wt. %, a hydrogel was formed at low temperature (FIG. 5 A, B). The thermo-responsive behavior was evaluated by rolling ball viscosimetry at different concentrations (10→15→20 wt. %) by a heating (5° C.→40° C.) and cooling (40° C.→5° C.) ramp. At 10 wt. % and 15 wt. %, the viscosity decreases steadily with increasing the temperature ($\eta_{5°\ C.}$(10 wt. %)=9 mPas→$\eta_{40°\ C.}$(10 wt. %)=3 mPas, $n_{5°\ C.}$(15 wt. %)=50 mPas→$n_{40°\ C.}$(10 wt. %)=11 mPas) without any notable features. The cooling and heating ramps yield similar values. In contrast, at 20 wt. % the viscosity increases very fast below a critical temperature of ~22° C., eventually trapping the ball, whereupon no further values are obtained (FIG. 5 C, D). Increasing again the temperature, the polymer solution again flows freely forming a viscous solution with dynamic viscosity values of ~70 mPas at 40° C. No notable hysteresis was observed in this experiment.

FIG. 5 demonstrates that an increasing concentration of A-PPhenOx-A leads to hydrogel formation. A) Pictures of aqueous solutions at 5° C. and different polymer concentrations (10→15→20 wt. %). B) Pictures of aqueous solutions at 5° C. and 40° C. and a polymer concentration of 20 wt. %. C, D) Results of temperature dependent viscosity measurements (rolling ball system).

As previously mentioned, stimuli responsive hydrogels have been utilized in different biomaterials applications (Sood, N.; Bhardwaj, A.; Mehta, S.; Mehta, A., Stimuli-Responsive Hydrogels in Drug Delivery and Tissue Engineering. Drug Delivery 2016, 23 (3), 748-770). Recently, different approaches were established to overcome limitations in the so-called biofabrication window, especially in bioprinting (Malda, J.; Visser, J.; Melchels, F. P.; Jüngst, T.; Hennink, W. E.; Dhert, W. J. A.; Groll, J.; Hutmacher, D. W., 25th Anniversary Article: Engineering Hydrogels for Biofabrication. Advanced Materials 2013, 25 (36), 5011-5028). One approach is to improve printability by support materials and sacrificial materials, while retaining cell viability utilizing biological components, cell-friendly crosslinking and mild printing conditions. The search for suitable hydrogel platforms is an ongoing challenge due to many specific and sometimes contradictive requirements. Appropriate gelation kinetics, good printability and cytocompatibility are key requirements for hydrogels during bioink design. Therefore, the viscoelastic properties of the present inverse thermogelling platform were thoroughly investigated via rheology. In the pronounced viscoelastic region (LVE, end of LVE marked with red line) a constant storage modulus G' of 14.8±0.3 kPa was obtained with low damping factor of 0.3±0.02, which suggest a stable viscoelastic solid-like hydrogel (FIG. 6 A). Interestingly the hydrogel exhibits a strong frequency dependency (FIG. 6 B). Increasing the frequency leads to increasing G' and decreasing G" values, i.e. the solid-like character is amplified with the dampening factor reaching values <0.03 at 500 s-1. To utilize a hydrogel as 3D-printable ink in different printing applications, three major rheological considerations must be addressed, namely pronounced shear thinning, defined force resistance and fast structure recovery properties (Naomi, P.; Willi, S.; Thomas, B.; Ferry, M.; Jürgen, G.; Tomasz, J., Proposal to Assess Printability of Bioinks for Extrusion-Based Bioprinting and Evaluation of Rheological Properties Governing Bioprintability. Biofabrication 2017, 9 (4), 044107). With increasing shear rate, the viscosity of the present hydrogel decreases following a power law expression with a flow index of 0.05±0.004, indicating very pronounced shear-thinning (FIG. 6 C). Even at very low shear rates of 0.001 1/s no viscosity plateau is reached and shear stress values of ca. 200 Pa are measured at this point. In contrast, at very high shear rates of 1000 1/s the viscosity values are very low (ca. 1 Pas) with shear stress values increasing up to 750 Pa. To obtain the yield point and the force resistance of the hydrogel, the viscosity was plotted as a function of the applied shear stress. Below the critical stress, almost constant viscosity values between $10^4$ and $10^5$ Pas with very low shear rates (between $10^{-4}$ and $10^{-5}$ $^1$/s) were determined. At a certain stress, defined as the yield point, the viscosity drops very fast to low viscosity values by subsequently increasing shear rate values (FIG. 6 D). The onset of 305 Pa is determined via two tangents. At high shear stress values of 800→1500 Pa a viscosity and shear rate plateau of 0.1 Pas and $10^3$→$10^4$ $^1$/s are reached, respectively. Structure recovery was tested using a 3 step test, designed as ORO (oscillation-rotational-oscillation) and ROR (rotational-oscillation-rotational) experiments, altering low and high strain regimes (FIG. 6 E, F). In both cases, the structure recovered very fast and the initial values where obtained during the experiments, which we interpret to show complete structure recovery. To obtain insights into the hydrogel morphology, cryogenic scanning electron microscopy (cryoSEM) was conducted (FIG. 6 G-I). A rather homogenous porous structure with pores in the range of several hundred nanometers was observed, which is in agreement with the fast gelation kinetics and rheological properties of a strong and stable hydrogel. In comparison to a recently described UCST-type hydrogel based on A-PPheOzi-A triblock copolymer (L. Hahn et al., Inverse Thermogelation of Aqueous Triblock Copolymer Solutions into Macroporous Shear-Thinning 3D Printable Inks ACS Appl. Mater. Interfaces 2020, 12, 11, 12445-12456), the novel A-PPhenOx-A hydrogel has significantly smaller pores. In summary, the novel hydrogel showed promising viscoelastic characteristics for bioprinting.

FIG. 6 shows the rheological characterization for dispense plotting applications and cryoSEM analysis of A-PPhenOx-A hydrogel at 5° C. A) Amplitude sweep of 20 wt. % hydrogel at 5° C. and an angular frequency of 10 rad/s with storage moduli (G'□), loss moduli (G"=o) and loss factor (■) shown. B) Frequency sweep with fixed amplitude of 0.1%. C) Viscosity (Δ) and shear stress (■) in dependency of the applied shear rate for a 20 wt. % hydrogel. D) Viscosity (Δ) and shear rate (■) as a function of applied shear stress in steady shear stress experiment. E) ORO (oscillation-rotational-oscillation) recovery test of hydrogel. F) ROR (rotational-oscillation-rotational) 3 step recovery. G-I) Cryo-SEM images of 20 wt. % hydrogel at 1k×→2k× →10k× magnification.

Based on favorable rheological properties, the printability of the hydrogel was investigated using extrusion based printing. First the achievable resolution was investigated by decreasing the layer distance from 2→1.5→1→0.75→0.5 mm (FIG. 7). Even at a layer distance of 0.75 mm, every individual layer could be distinguished and no strand fusion was observed. Additionally, the filament collapse test was investigated (Ribeiro, A. et al., Biofabrication 2017, 10 (1), 014102). A freehanging hydrogel bridge of a total distance of 1.7 cm could be realized without significant strand sag (FIG. 8 B). Based on that results a first real 3D construct was printed (FIG. 7). A 20-layered cylindrical construct with a diameter of 5 mm and a total height of 5 mm was printed. The structure stayed intact and no significant collapse was observed.

FIG. 7 shows the results of direct ink-writing of a 20 wt. % hydrogel and a hybrid hydrogel (composition: 20 wt. % of the block copolymer in accordance with the invention and 1 wt. % alginate) at 8-10° C. (Nozzle 25 G, speed: 10 mm/s). Only by combining the disclosed polymer with the 1 wt. % alginate, the alginate could be printed in three dimensions. A), E) Filament fusion test to visualize printing resolution. B), F) Filament collapse test by printing bridges of increasing distances. C), D), G), H) Printed 20 layer (5×5 mm cylindrical tube structures) constructs. A)-D) 20 wt. % hydrogel containing the described polymer. E)-H) 20 wt. % described polymer and 1 wt. % alginate. G), H) After crosslinking with $CaCl_2$) and incubation at 37° C. in aqueous solution.

Finally, a bioprinting process was performed and the cytocompatibility was investigated using NIH 3T3 cells (FIG. 8). After dissolving the block copolymer in accordance with the invention, alginate and dispersing cells at 37° C. in cell culture medium, the bioink was processed at 8 ° C. The cell viability was analyzed using automatic cell counting in three fluorescence images (n=3) of 3 biological replicates (n=3) obtained with an epifluorescence microscope (Zeiss Observer, Germany).

No notable cytotoxicity was observed for the compositions comprising the block copolymer in accordance with the invention and excellent cell viability of >95% was obtained.

$M_n$($1^{st}$ block): 1.8 kg/mol, ⊗($1^{st}$ block): 1.05

$M_n$($2^{nd}$ block): 2.9 kg/mol, ⊗($2^{nd}$ block): 1.08

Figure 1:
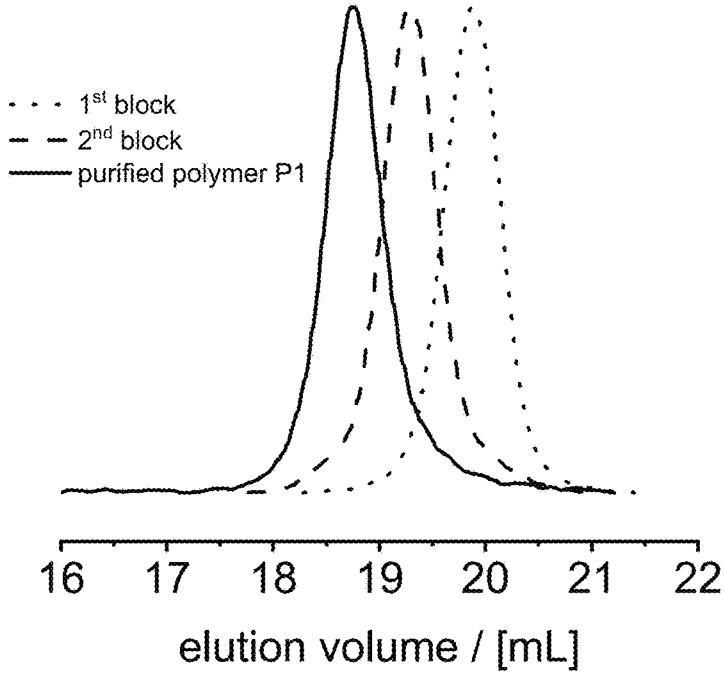
FIG. 1 shows GPC-Traces after every block and the purified ABA-triblock copolymer P1.
Figure 2:
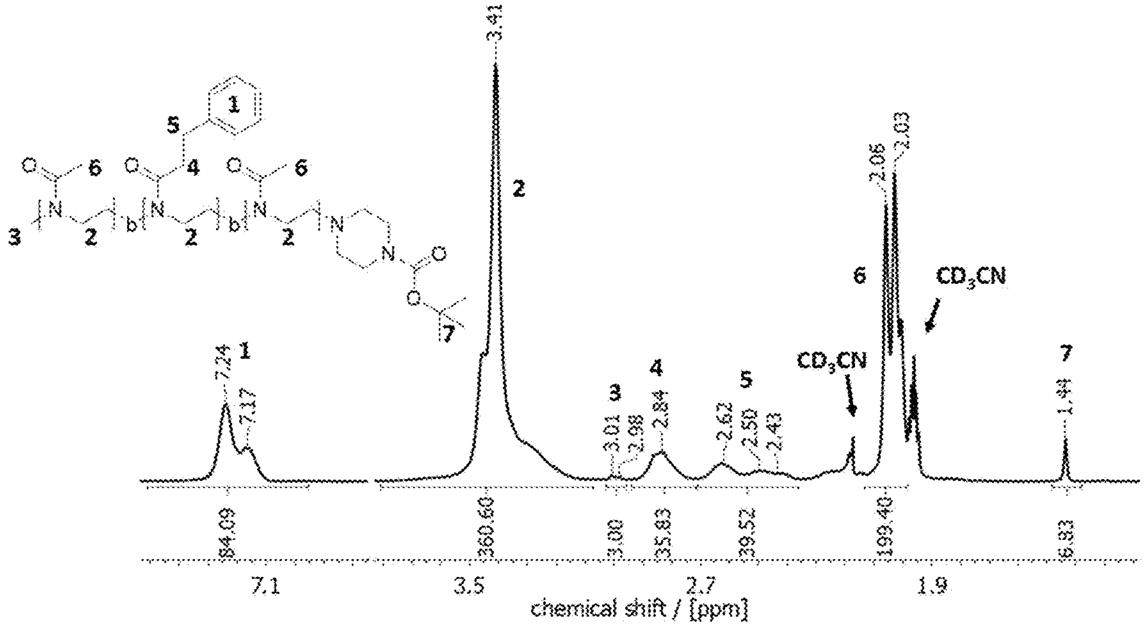

FIG. 2 shows the $^1$H-NMR of purified ABA-triblock copolymer Me-$PMeOx_{37}$-b-$PPhenOx_{17}$-b-$PMeOx_{36}$-Pip-Boc (Mw: 9.4 kg/mol, PMeOx/PPhenOx: 4.3) in $CD_3CN$.

Figure 3:
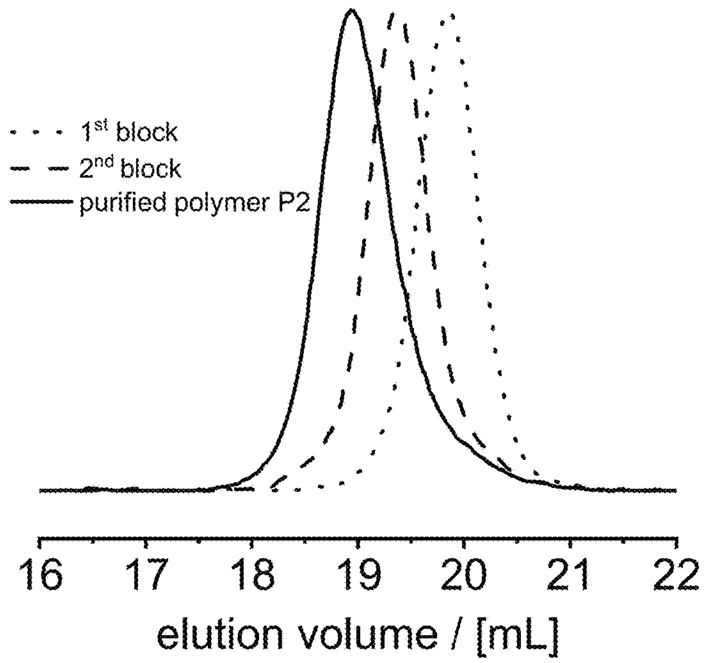

FIG. 3 shows GPC-Traces after every block and the purified ABA-triblock copolymer P2. $M_n$($1^{st}$ block): 2.3 kg/mol, ⊗($1^{st}$ block): 1.08 $M_n$($2^{nd}$ block): 3.3 kg/mol, ⊗($2^{nd}$ block): 1.12

Figure 4:
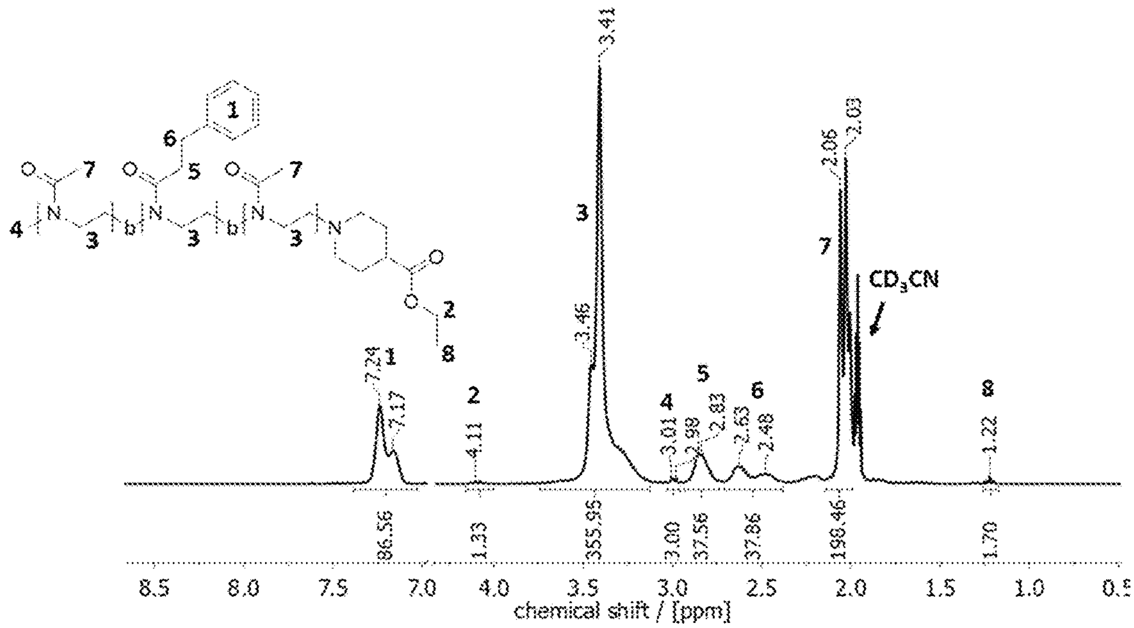

FIG. 4 shows the $^1$H-NMR of purified ABA-triblock copolymer Me-$PMeOx_{36}$-b-$PPhenOx_{17}$-b-$PMeOx_{36}$-EIP (Mw: 9.3 kg/mol, PMeOx/PPhenOx: 4.1) in $CD_3CN$.

Figure 5:
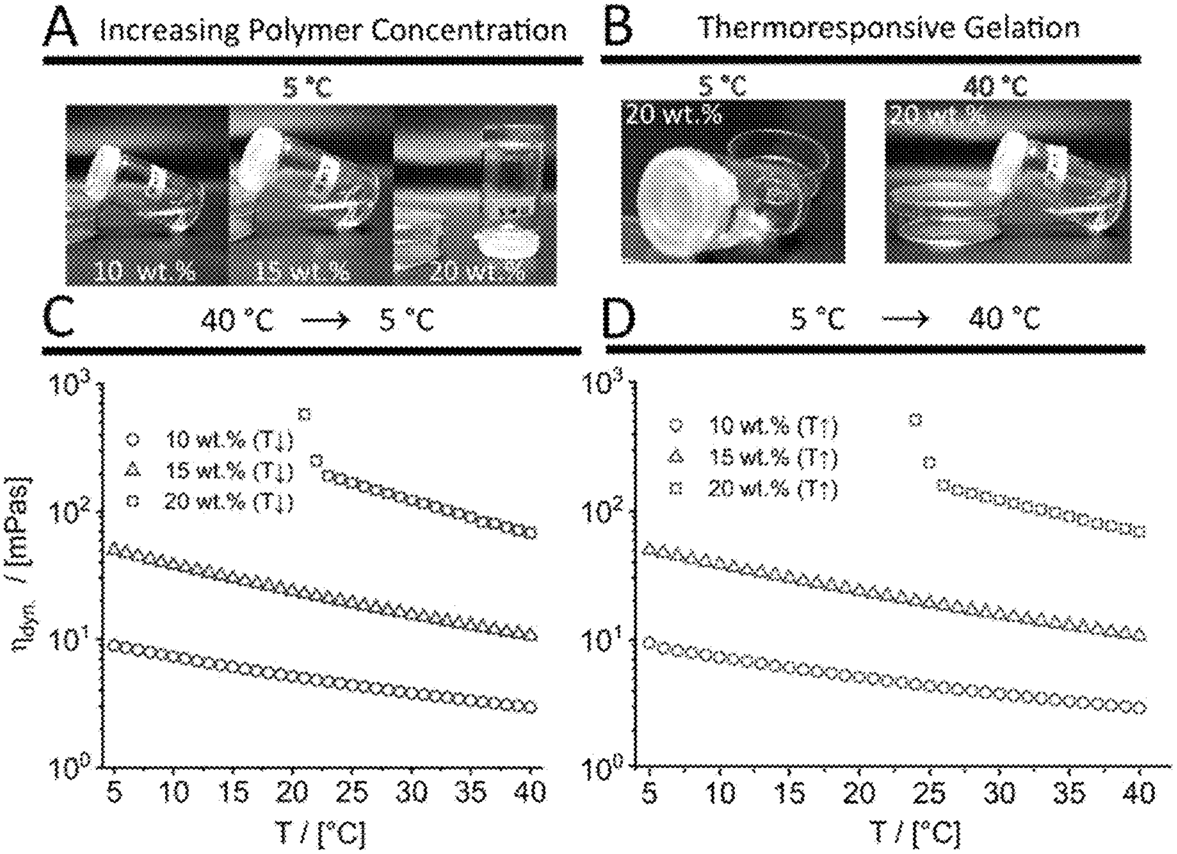

FIG. 5 shows that an increasing concentration of A-PPhenOx-A leads to hydrogel formation. A) Pictures of aqueous solutions at 5° C. and different polymer concentrations (10→15→20 wt. %). B) Pictures of aqueous solutions at 5° C. and 40° C. and a polymer concentration of 20 wt. %. C,D) Temperature dependent viscosity measurements (rolling ball system).

Figure 6:
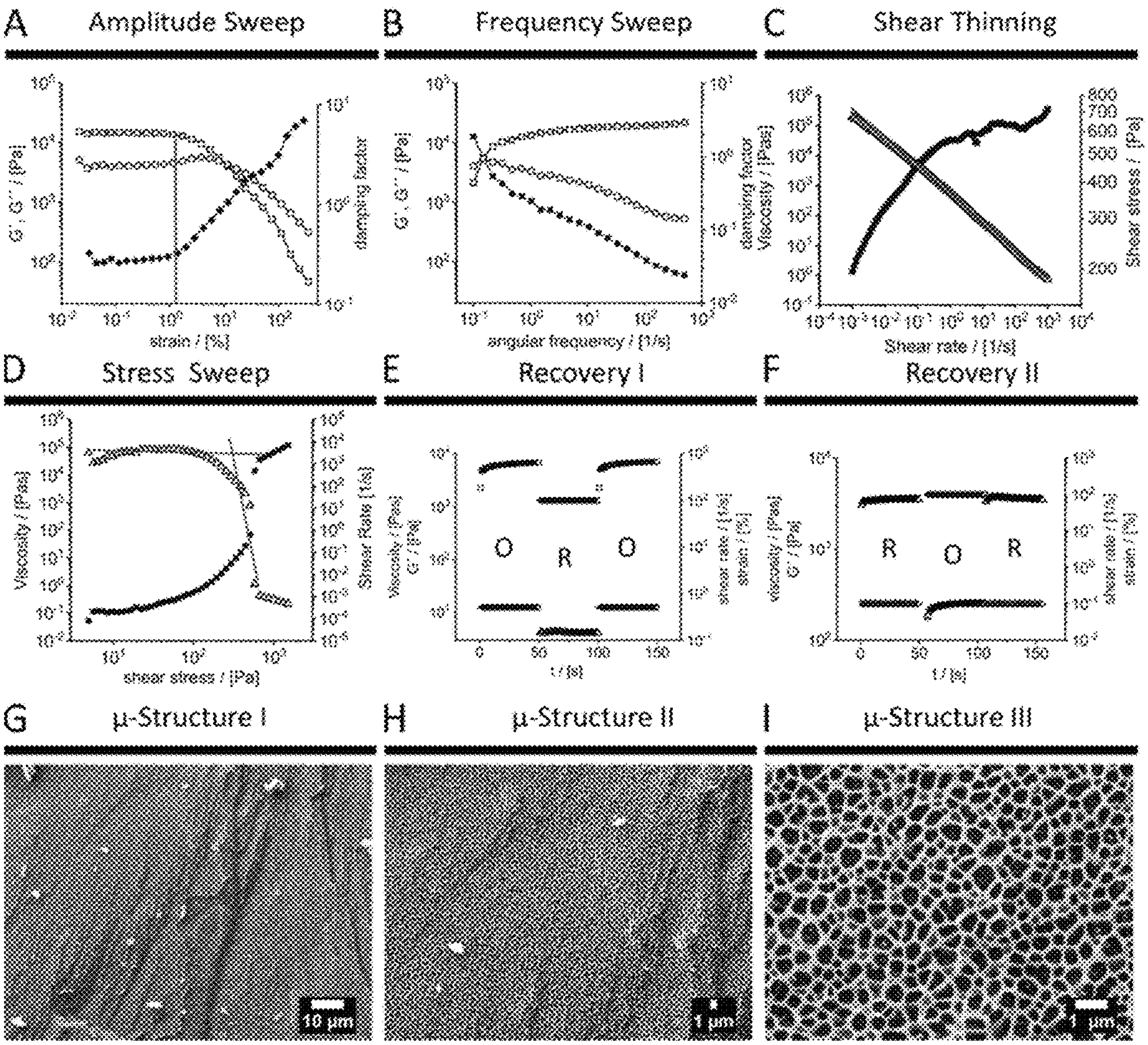

FIG. 6 shows the results for the rheological characterization for dispense plotting applications and cryoSEM analysis of A-PPhenOx-A hydrogel at 5° C. A) Amplitude sweep of 20 wt. % hydrogel at 5° C. and an angular frequency of 10 rad/s with storage moduli (G'□), loss moduli (G"=o) and loss factor (■) shown. B) Frequency sweep with fixed amplitude of 0.1%. C) Viscosity (Δ) and shear stress (■) in dependency of the applied shear rate for a 20 wt. % hydrogel. D) Viscosity (Δ) and shear rate (■) as a function of applied shear stress in steady shear stress experiment. E) ORO (oscillation-rotational-oscillation) recovery test of hydrogel. F) ROR (rotational-oscillation-rotational) 3 step recovery. G-I) Cryo-SEM images of 20 wt. % hydrogel at 1k×→2k×→10k×magnification.

Figure 7:
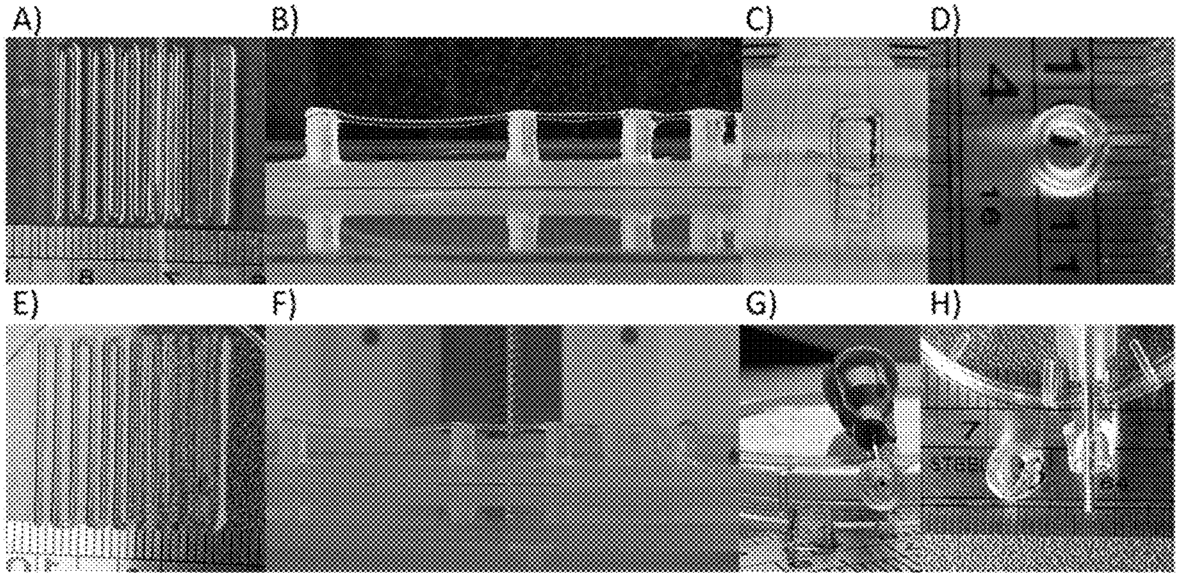

FIG. 7 shows the results of direct ink-writing of a 20 wt. % hydrogel and a hybrid hydrogel (composition: 20 wt. % of the block copolymer in accordance with the invention and 1 wt. % alginate) at 8-10° C. (Nozzle 25 G, speed: 10 mm/s). A), E) Filament fusion test to visualize printing resolution. B), F) Filament collapse test by printing bridges of increasing distances. C), D), G), H) Printed 20 layer (5×5 mm cylindrical tube structures) constructs. A)-D) 20 wt. % hydrogel containing the described polymer. E)-H) 20 wt. % described polymer and 1 wt. % alginate. G), H) After crosslinking with $CaCl_2$) and incubation at 37° C. in aqueous solution.

Figure 8:
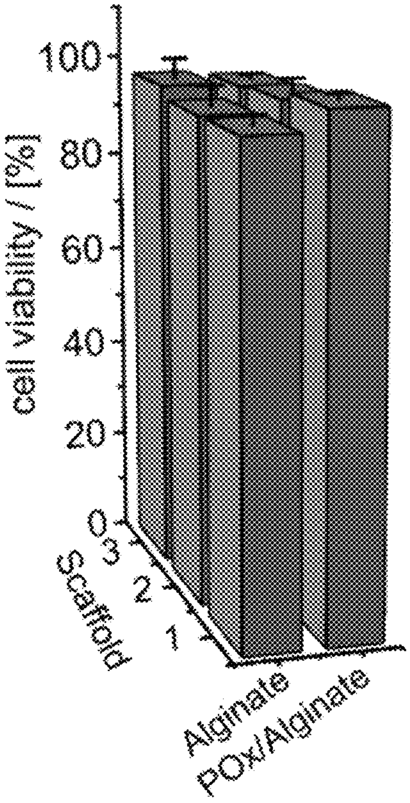

FIG. 8 summarizes the results of a bioprinting process and the analysis of cytocompatibility using NIH 3T3 cells. After dissolving the block copolymer in accordance with the invention, alginate and dispersing cells at 37° C. in cell culture medium, the bioink was processed at 8° C. The cell viability was analyzed using automatic cell counting in three fluorescence images (n=3) of 3 biological replicates (n=3) obtained with an epifluorescence microscope (Zeiss Observer, Germany).

The invention claimed is:

1. A block copolymer comprising:

a polymer block (A) comprising repeating units of formula (I):

(I)

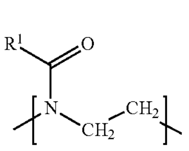

wherein $R^1$ is methyl or ethyl, and a polymer block (B) comprising repeating units of formula (II):

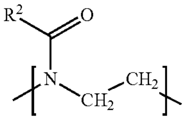

(II)

wherein $R^2$ represents a group $—CH_2—CH_2$-phenyl.

2. The block copolymer of claim 1, wherein the number of repeating units of formula (I) in each polymer block (A) is 5 or more and 100 or less, and wherein the number of repeating units of formula (I) is independently 5 or more and 100 or less for each polymer block (A) if more than one polymer block (A) is present.

3. The block copolymer of claim 1, wherein the number of repeating units of formula (II) in each polymer block (B) is 5 or more and 100 or less, and wherein the number of repeating units of formula (II) is independently 5 or more and 100 or less for each polymer block (B) if more than one polymer block (B) is present.

4. The block copolymer of claim 1, wherein the ratio of the total number of repeating units of formula (I) in the polymer block (A) to the total number of repeating units of formula (II) in the polymer block (B) is in the range of 20:1 to 1:1.

5. The block copolymer of claim 1, wherein the degree of polymerization of the block copolymer is in the range of 40 to 180.

6. The block copolymer of claim 1, wherein the block copolymer is a di- or triblock copolymer.

7. The block copolymer of claim 1, wherein the block copolymer comprises a triblock copolymer of two polymer blocks (A) and one polymer block (B) having the structure (A)-(B)-(A).

8. A hydrogel composition comprising the block copolymer of claim 1.

9. The hydrogel composition of claim 8, further comprising one or more further hydrogel forming polymers.

10. The hydrogel composition of claim 9, wherein the one or more further hydrogel forming polymers are selected from the group consisting of alginate, gelatin, silk protein, collagen, fibrin, and cellulose.

11. The hydrogel composition of claim 8, further comprising viable cells.

12. The block copolymer of claim 1, wherein the block copolymer comprises at least a portion of a support material or a structural material in 3D printing, or as an internal sacrificial support material in 3D printing.

13. The hydrogel composition of claim 8, wherein the hydrogel composition comprises a bioink.

14. A method for the provision of a hydrogel scaffold having a geometry, the method comprising subjecting a composition comprising the block copolymer of claim 1 to 3D printing.

15. A method for the provision of an artificial tissue, the method comprising forming a hydrogel scaffold comprising viable cells from the hydrogel composition of claim 11.

* * * * *